United States Patent [19]

Yee

[11] 4,257,771

[45] Mar. 24, 1981

[54] PROCESS FOR MEASURING LECITHIN CONCENTRATION IN BIOLOGICAL FLUIDS

[76] Inventor: Hugh Yee, 4201 Frostwood, Troy, Mich. 48098

[21] Appl. No.: 34,597

[22] Filed: Apr. 30, 1979

[51] Int. Cl.³ .................... G01N 33/92; G01N 31/08
[52] U.S. Cl. .................................. 23/230 B; 210/656
[58] Field of Search ..................... 23/230 B; 210/31 C

[56] References Cited

PUBLICATIONS

Chemical Abstracts, 80:105,486t (1974).
V. Giridhar et al., Clin. Chem., 20 (4), 513–514 (1974).
Chemical Abstracts, 84:101783x (1976).
Chemical Abstracts, 85:74417t (1976).
Chemical Abstracts, 76:117839r (1972).

*Primary Examiner*—Sidney Marantz
*Attorney, Agent, or Firm*—Harry R. Dumont

[57] ABSTRACT

A process for determining lecithin concentration in biological fluids such as blood and amniotic fluids including the steps of separating the lecithin from the fluid and isolating the separated lecithin from similar phospholipids by column chromatography. The separated lecithin is then hydrolyzed and formed into chromogens. The evaluation of the concentration of the lecithin is done by spectrophotometric measurement.

9 Claims, No Drawings

PROCESS FOR MEASURING LECITHIN CONCENTRATION IN BIOLOGICAL FLUIDS

BACKGROUND OF THE INVENTION

The synthesis and release of phospholipids in the lungs is an important factor for fetal lung maturity. The phospholipids contribute to the stability of the peripheral airways by inhibiting the collapse of alveoli at low lung volume during expiration. They also act as an anti-edema factor by inhibiting the exudation of liquid from the pulmonary circulation into the airways. Lung surfactant can be recovered either from endobrachial lavage fluid or isolated from lung homogenate. The purified complex contains 85-95% lipid and 10-20% protein. About 90-95% w/w of the lipids are phospholipids with the remainder being cholesterol.

Lecithin (Phosphatidyl choline) has been recognized as the principal component accounting for 60-90% of the total phospholipids with sphingomyelin, phosphatidyl ethanolamine, phosphatidyl serine, lysolecithin, phosphatidyl inositol, and phosphatidyl glycerol comprising the remaining amount. The majority of these phospholipids are saturated, i. e., the two fatty acid residues contain no double bonds. The predominant fatty acid is palmitic acid (16:0). The dipalmitoyl lecithin derivative is the major surface active material, and it is acetone insoluble. It is well established that the gestational age of the fetus may be estimated by measuring the amounts of phosopholipids in the amniotic fluid. Louis Gluck, et al., *American Journal Obstetrics & Gynecology*, 109, 440-445, 1971, introduced the lecithin/sphingomyelin (L/S) ratio. This measurement was carried out by centrifugation of the amniotic fluid, cold acetone precipitation, thin layer chromatography, sulfuric acid charring of the separated phospholipids, and densitometry. This particular approach and its many modifications are the most widely used ones for assessing fetal lung maturity.

The quantitative measurement of phosphatidyl choline (lecithin) in amniotic fluid was described by S.G. Bhagwanani, et al., *The Lancet* 2, 66-67, 1972. The phospholipids were extracted with 2:1 chloroform-methanol, separated by thin layer chromatography, and following removal from the silica gel and digestion with perchloric acid, quantitated by phosphate measurement. These referred to methods, however, have the disadvantage of being time consuming and technically more difficult to carry out.

SUMMARY OF THE INVENTION

The present invention pertains to a process for determining lecithin concentration in biological fluids, in particular, amniotic fluid utilizing known spectrophotometric procedures wherein the phospholipids are extracted from the fluid, separated by a column chromatographic step, hydrolyzed with acidic periodate, and formed into chromogens which are measured. The present method for determining lecithin overcomes the disadvantages of the prior art by providing a relatively simple procedure whereby the lecithin content of a biological fluid sample may be analyzed with maximum speed, accuracy, and efficiency manually.

DESCRIPTION OF THE PREFERRED EMBODIMENT

According to the present invention, lecithin may initially be separated from the fluid by one of the following procedures:

(a) the lecithin may be separated from the fluid by extraction with chloroform-methanol;

(b) the lecithin may be separated from the fluid by extraction with ethanol-ethyl ether.

Following the separation of the lecithin from the fluid sample, the lecithin is isolated from the other similar phospholipids by passage of a extract through a column containing a specific adsorbent material. After washing the column with methanol to complete removal of the lecithin, the collected combined solvents are evaporated to yield a residue comprised of lecithin.

The lecithin molecule is hydrolyzed to release inorganic phosphate by utilizing a chemical mixture of periodic acid and ethanol in a sulfuric acid solution. The hydrolyzed lecithin is then diluted with water for chromogen formation.

The chromogen development may then be accomplished by reaction of the liberated phosphate derived from lecithin with ammonium molybdate. This reaction is followed by reduction using stannous chloride with hydrazine sulfate. Spectrophotometric measurements may then be made at 660 nm.

According to the present invention, the concentration of lecithin present in the fluid is determined by comparison of the absorbance values of the fluid sample with those of lecithin or inorganic phosphate standards of known concentration.

The practice of the present invention is further illustrated by reference to the following detailed examples:

EXAMPLE I

Separation of the lecithin from fluid

A separation of the lecithin from the sample may be effected by any one of the following procedures:

(a) According to the first procedure, an amniotic fluid sample of 1 ml may be extracted with 4 ml of a 2:1 (v/v) chloroform-methanol solvent. Blood plasma or serum samples of 0.075 ml may be extracted with 3 ml of the 2:1 chloroform-methanol. The samples are vortexed for 1 minute to effect the extraction. The mixtures are then centrifuged and the solvent layers separated and transferred to a clean test tube.

(b) In an alternative method, all directions are identical to (a) with the exception that a solvent of ethanolethyl ether 3:1 (v/v) is substituted for the 2:1 (v/v) chloroform-methanol.

Column Chromatography

The solvent extracts are passed through 0.100 g calcium hydroxy phosphate (hydroxyl apatite) in a glass column of 180×5.8 mm dimensions and 4 ml capacity. The column is constructed by inserting a polyethylene filler disc into the glass column as a support for the adsorbent, followed by diethylaminoethyl cellulose (DEAE) or triethylaminoethyl cellulose (TEAE) to a height of ⅛', and then the 0.100 g of calcium hydroxy phosphate. A small amount of glass wool is inserted at the top of the column to prevent column breakage when solvent is initially introduced. The solvents are collected in a tube. The column is then eluted with 4 ml methanol which is collected in the same tube used for the extraction solvent. The combined solvent is evaporated at 55° C. until dry.

Other adsorbents which may be substituted for the calcium hydroxy phosphate (hydroxyl apatite) are: diethylaminoethyl cellulose, triethylaminoethyl cellulose, silica gel, and silicic acid.

Hydrolysis

The lecithin obtained from the fluid sample by means of one of the described separation procedures is then hydrolyzed. The hydrolysis is affected by the addition of 1 ml of a "hydrolysis mixture" and heating at 100° C. for 45 minutes. The "hydrolysis mixture" consists of 3 ml of 5 mol/liter sulfuric acid, 1 mol 0.1 mol/liter periodic acid and 6 ml of ethanol. Following hydrolysis, the sample is diluted with 2 ml of water for chromogen development.

Chromogen Formation and Measurement

The chromogen formation and the spectrophotometric measurement may be carried out manually.

Manual method

According to the manual method, the diluted hydrolyzed lecithin solution, 0.5 ml, is transferred to a test tube. A blank consisting of reagents carried through the hydrolysis is prepared by removing a 0.5 ml aliquot and placing it in an appropriate tube. Comparative standards are prepared by pipeting into labeled tubes. The chromogen development is accomplished in the fluid samples and the lecithin standards by the addition of 2 ml of a 3% (w/v) ammonium molybdate in 5 mol/liter sulfuric acid to all tubes. After mixing, 1 ml of 0.03% (w/v) stannous chloride–0.3% (w/v) hydrazine sulfate is added to all tubes and mixed. The tubes are allowed to stand 5 minutes and the absorbance spectrum of the fluid sample obtained at 660 nm is compared against the reagent blank and the lecithin or phosphate standards of known concentration.

It is important to note that a number of adsorbents may be used in place of the calcium hydroxy phosphate (hydroxyl apatite) for the column chromatographic separation of lecithin. Other adsorbents which may be substituted are: diethylaminoethyl cellulose (DEAE), triethylaminoethyl cellulose (TEAE), silica gel, and silicic acid.

What is claimed is:

1. A process for determining the lecithin concentration in a biological fluid, comprising the steps of:
   (a) separating the lecithin from the fluid;
   (b) isolating the separated lecithin from similar phospholipids by passing the extract through a column containing a specific adsorbent material;
   (c) hydrolyzing the separated lecithin;
   (d) forming the separated lecithin into chromogens; and
   (e) evaluating the concentration of the lecithin by spectrophotometric measurement.

2. The process defined in claim 1 wherein the step of separating the lecithin is accomplished by extraction with chloroform-methanol.

3. The process defined in claim 1 wherein the step of separating the lecithin is accomplished by extraction with ethanol-ethyl ether.

4. The process defined in claim 1 wherein the step of hydrolyzing the separated lecithin is performed by a chemical mixture of periodic acid and ethanol in a sulfuric acid solution.

5. The process defined in claim 1 wherein the step of forming the separated lecithin into chromogens is performed by reaction of the liberated phosphate derived from the lecithin with ammonium molybdate.

6. The process defined in claim 5 wherein after the chromogen forming there is included the further step of reduction with stannous chloride and hydrazine sulfate.

7. The process defined in claim 1 wherein the evaluating of the concentration of the lecithin is determined by comparison of the absorbance values of the lecithin sample being measured with those of lecithin standards of known concentrations.

8. The process defined in claim 1 including the further step of diluting the hydrolyzed lecithin with water.

9. The process defined in claim 1 including washing the column with methanol to complete removal of the separated lecithin.

* * * * *